United States Patent
Baumgartner

(10) Patent No.: US 9,833,291 B2
(45) Date of Patent: Dec. 5, 2017

(54) ULTRASOUND CT REGISTRATION FOR POSITIONING

(75) Inventor: Adrian Baumgartner, Langendorf (CH)

(73) Assignee: DEPUY SYNTHES PRODUCTS, INC., Raynham, MA (US)

( * ) Notice: Subject to any disclaimer, the term of this patent is extended or adjusted under 35 U.S.C. 154(b) by 1226 days.

(21) Appl. No.: 13/523,155

(22) Filed: Jun. 14, 2012

(65) Prior Publication Data

US 2013/0150863 A1    Jun. 13, 2013

Related U.S. Application Data

(60) Provisional application No. 61/499,838, filed on Jun. 22, 2011, provisional application No. 61/499,849, filed on Jun. 22, 2011.

(51) Int. Cl.
*A61B 17/88* (2006.01)
*A61B 19/00* (2006.01)
(Continued)

(52) U.S. Cl.
CPC .............. *A61B 19/46* (2013.01); *A61B 6/12* (2013.01); *A61B 17/88* (2013.01); *A61B 17/8866* (2013.01); *A61B 34/20* (2016.02); *A61B 90/06* (2016.02); *G06T 7/33* (2017.01); *A61B 2034/2051* (2016.02);
(Continued)

(58) Field of Classification Search
CPC .............. A61B 17/8866; A61B 90/378; A61B 34/2063; A61B 2090/3916
USPC .......... 606/87, 102, 130; 600/407, 414, 417, 600/426, 429
See application file for complete search history.

(56) References Cited

U.S. PATENT DOCUMENTS 5,636,255 A    6/1997    Ellis
6,436,100 B1   8/2002    Berger
(Continued)

FOREIGN PATENT DOCUMENTS

CN    1406117    3/2003
CN    1950849    4/2007
(Continued)

OTHER PUBLICATIONS

Wein et al., "Automatic CT-ultrasound Registration for Diagnostic imaging and Image-Guided Intervention," Jun. 19, 2008, Medical Image Analysis, pp. 577-585.
(Continued)

*Primary Examiner* — David Bates
(74) *Attorney, Agent, or Firm* — Fay Kaplun & Marcin, LLP

(57) ABSTRACT

An assembly for manipulating a bone includes a first manipulating element configured to be attached to a first portion of bone and including a location emitting signal and a second manipulating element configured to be attached to a second portion of bone and including a sensor detecting the location emitting signal to provide a position and orientation signal of the first and second manipulating elements relative to one another. The assembly also includes a tracking unit including a processor tracking movement of the first and second manipulating elements relative to one another in a plurality of dimensions using the position and orientation signals.

12 Claims, 7 Drawing Sheets

(51) Int. Cl.
*A61B 6/12* (2006.01)
*G06T 7/33* (2017.01)
*A61B 34/20* (2016.01)
*A61B 90/00* (2016.01)

(52) U.S. Cl.
CPC . *A61B 2034/2063* (2016.02); *A61B 2090/363* (2016.02); *A61B 2090/364* (2016.02); *A61B 2090/378* (2016.02); *A61B 2090/397* (2016.02); *A61B 2090/3916* (2016.02); *A61B 2090/3945* (2016.02); *A61B 2090/3954* (2016.02); *G06T 2207/10081* (2013.01); *G06T 2207/10132* (2013.01); *G06T 2207/30008* (2013.01); *G06T 2207/30204* (2013.01)

(56) References Cited

U.S. PATENT DOCUMENTS

| | | | |
|---|---|---|---|
| 6,877,239 | B2 | 4/2005 | Leitner et al. |
| 7,244,234 | B2 | 7/2007 | Ridley et al. |
| 7,862,570 | B2 | 1/2011 | Russell et al. |
| 8,180,429 | B2 * | 5/2012 | Sasso ............................ 600/424 |
| 8,239,001 | B2 * | 8/2012 | Verard .................... A61B 5/062 600/407 |
| 2002/0085681 | A1 | 7/2002 | Jensen |
| 2004/0152970 | A1 | 8/2004 | Hunter et al. |
| 2005/0033149 | A1 | 2/2005 | Strommer et al. |
| 2005/0124988 | A1 | 6/2005 | Terrill-Grisoni et al. |
| 2006/0015031 | A1 | 1/2006 | Kienzle, III |
| 2007/0123912 | A1 * | 5/2007 | Carson .......................... 606/130 |
| 2008/0013814 | A1 | 1/2008 | Carlsen |
| 2008/0147078 | A1 | 6/2008 | Francis et al. |
| 2008/0249394 | A1 * | 10/2008 | Giori et al. ................... 600/407 |
| 2008/0306490 | A1 * | 12/2008 | Lakin et al. .................. 606/130 |
| 2009/0000627 | A1 * | 1/2009 | Quaid et al. .................. 128/898 |
| 2010/0312247 | A1 | 12/2010 | Tuma |
| 2011/0257653 | A1 * | 10/2011 | Hughes et al. ................. 606/79 |

FOREIGN PATENT DOCUMENTS

| | | |
|---|---|---|
| CN | 101305395 | 11/2008 |
| EP | 1925256 | 5/2008 |
| JP | 2001-061861 | 3/2001 |
| JP | 2006-513011 | 4/2006 |
| JP | 2008-055156 | 3/2008 |
| WO | 2004/046754 | 6/2004 |
| WO | 2010/025575 | 3/2010 |
| WO | 2010/111224 | 9/2010 |

OTHER PUBLICATIONS

Barratt et al. "Self-calibrating Ultrasound-to-CT Bone Registration", Medical Image Computing and Computer-Assisted Intervention—MICCAI 2005, Lecture Notes in Computer Science vol. 3749, 2005, pp. 605-612.

Lavallee et al., "Computer-Assisted Spinal Surgery Using Anatomy-Based Registration", in: Computer-integrated Surgery: technology and clinical applications, eds. R. Taylor, et al., Boston, Massachusetts: Academic Press, 1996, pp. 425-449.

* cited by examiner

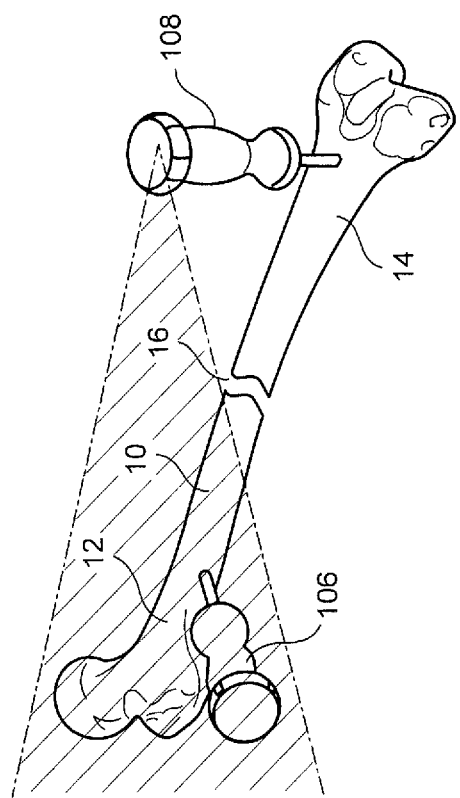
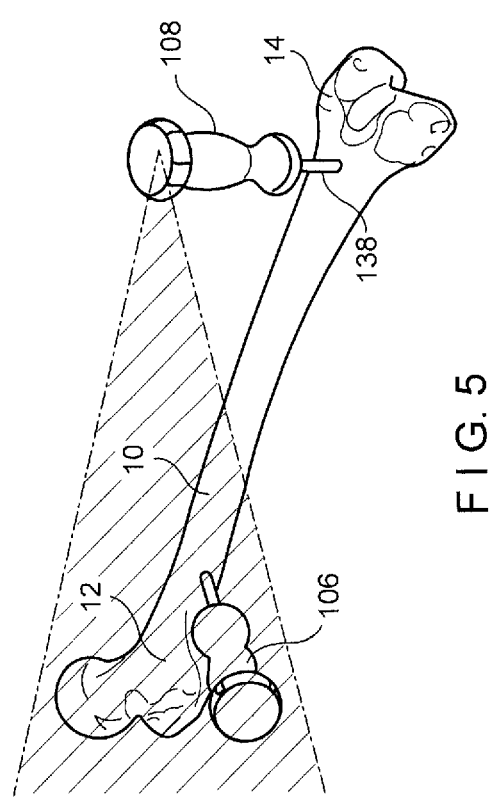

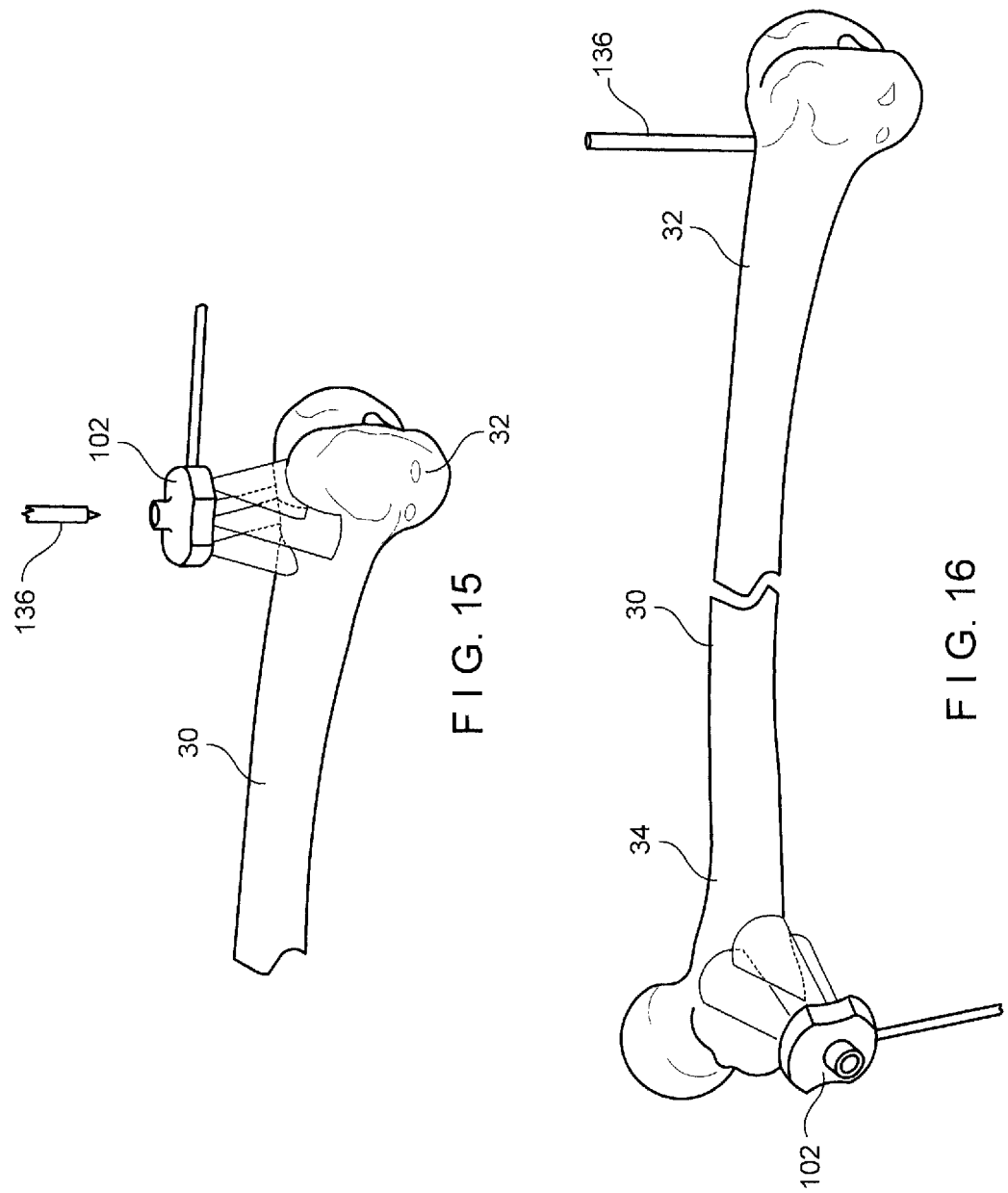

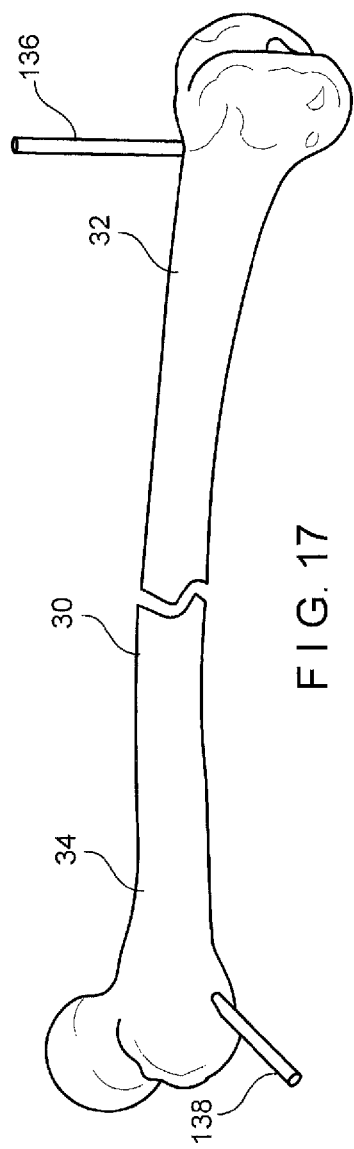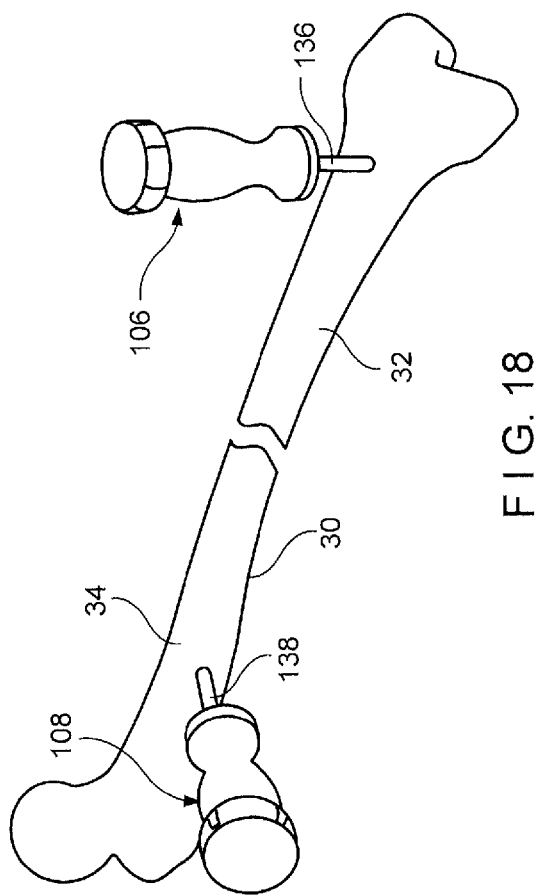

US 9,833,291 B2

ULTRASOUND CT REGISTRATION FOR POSITIONING

PRIORITY CLAIM

The present application claims priority to U.S. Provisional Application Ser. No. 61/499,849 entitled "Ultrasound CT Registration for Positioning" filed on Jun. 22, 2011 and U.S. Provisional Application Ser. No. 61/499,838 entitled "Ultrasound CT Registration for Positioning" filed on Jun. 22, 2011, the entire disclosures of which are incorporated herein.

BACKGROUND

CT (Computed Tomography) is often used to image bones as this permits the construction of high definition three-dimensional images. These high definition images facilitate understanding of fractures, ligament injuries and dislocations and assist in the formulation of treatment strategies. CT scanners, however, are large, bulky devices which are inconvenient for use during treatment procedures. Ultrasound imaging devices are less bulky and more convenient for use during procedures. However, the images produced by these devices are less accurate and comprehensive than those produced by CT scanners and, consequently, have been of limited utility in procedures requiring precision.

SUMMARY OF THE INVENTION

The present invention relates to an assembly for manipulating a bone, comprising a first manipulating element configured to be attached to a first portion of bone and including a location emitting signal and a second manipulating element configured to be attached to a second portion of bone and including a sensor detecting the location emitting signal to provide a position and orientation signal of the first and second manipulating elements relative to one another. The assembly also comprises a tracking unit including a processor tracking movement of the first and second manipulating elements relative to one another in a plurality of dimensions using the position and orientation signals.

BRIEF DESCRIPTION OF THE DRAWINGS

FIG. 5 shows a perspective view of the bone of FIG. 2, with a second handle mounted on the second portion of bone;

FIG. 6 shows a perspective view of the bone of FIG. 2, with a cut formed therein such that the first and second portions of bone may be manipulated relative to one another;

FIG. 15 shows a perspective view of a fractured bone to be treated according to another exemplary embodiment of the present invention, using the system of FIG. 1;

FIG. 16 shows a perspective view of the bone of FIG. 15, with a first marker inserted through a first fractured portion thereof;

FIG. 17 shows a perspective view of the bone of FIG. 15, with a second marker inserted through a second fractured portion thereof; and FIG. 18 shows a perspective view of the bone of FIG. 15, with first and second handle elements attached to first and second fractured portions, respectively.

DETAILED DESCRIPTION

Figure 1:
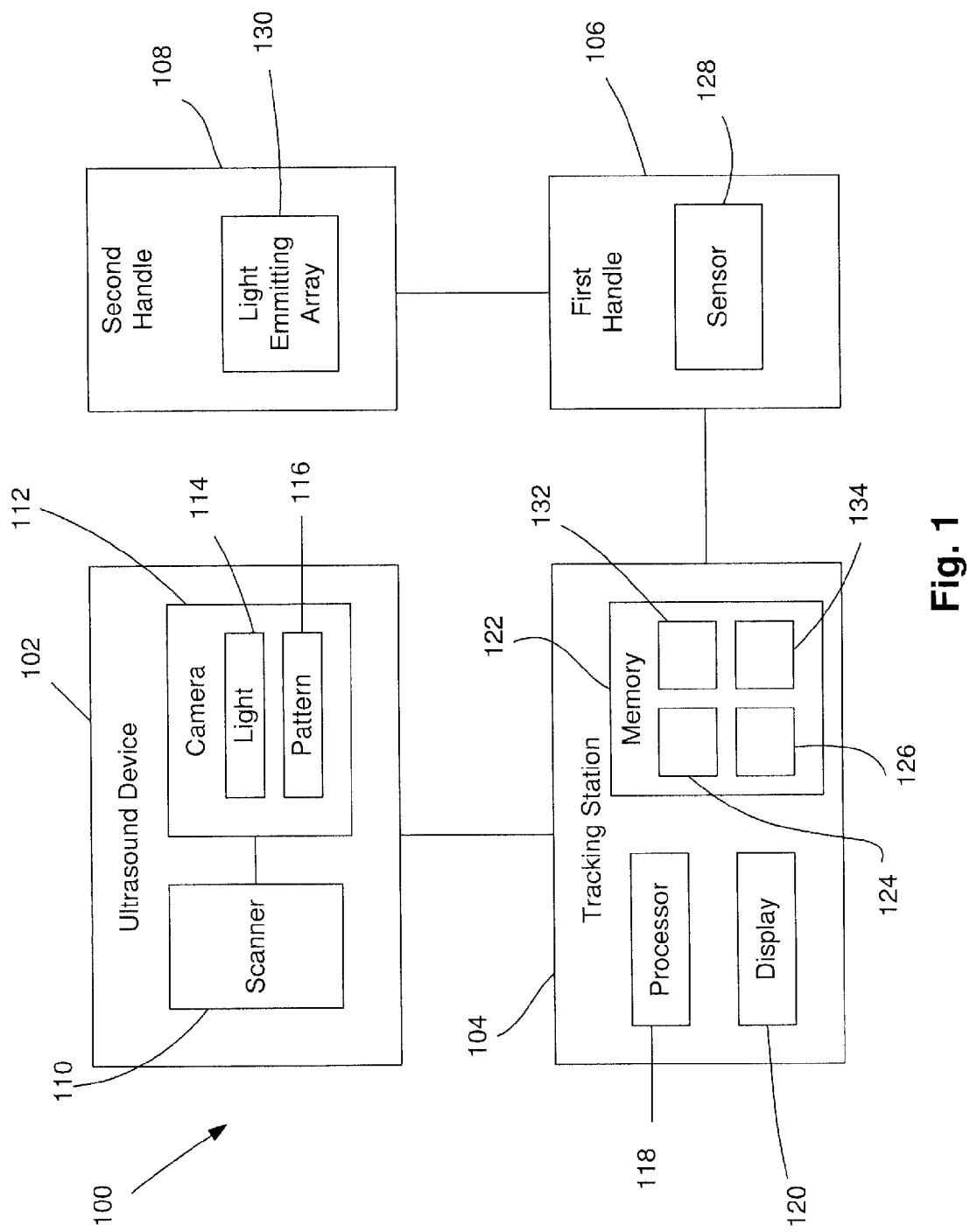
FIG. 1 shows a schematic drawing of a system according to an exemplary embodiment of the present invention.

The present invention may be further understood with reference to the following description and the appended drawings, wherein like elements are referred to with the same reference numerals. The present invention relates to a system and method for treating bones and, in particular, relates to a system and method for using registered ultrasound and CT data indicating a position of one or more markers on a bone so that ultrasound data obtained during a treatment procedure may be employed to aid in manipulating previously obtained CT image data to accurately track the position of one or more portions of the bone during a procedure. Exemplary embodiments of the present invention describe a system and method for referencing data which is registered to CT image data to establish the location within the CT image of a first handle element coupled to a first portion of bone so that data obtained as the first portion of bone is manipulated via the first handle element may be used to manipulate the CT image to show the movement of the first portion of bone. A second handle element may be coupled to a second portion of bone so that registered data indicating relative positions of the first and second handle elements may be used to manipulated the CT image in real time to show the relative movement of first and second portions of bone. It will be understood by those of skill in the art that, although the exemplary embodiments describe first and second handle elements coupled to first and second portions of a bone, respectively, the first and second handle elements may also be positioned on first and second bones or on any other substantially rigid body structures so that previously obtained CT image data of the structures may be manipulated to show motion of the structures during a procedure.

As shown in FIG. 1, a system 100 according to an exemplary embodiment of the present invention comprises a portable ultrasound device 102 configured to obtain and transmit ultrasound data 124 (e.g., ultrasound image data) of a bone to a tracking station 104 which registers the ultrasound data 124 with CT data 126 (e.g., CT image) obtained prior to the collection of the ultrasound data 124 to determine a location of a first handle element 106 relative to the CT data 126. The ultrasound device 102 includes an ultrasound scanner 110 for obtaining the ultrasound data 124 of the bone and a camera 112 facilitating optical tracking of a position of the first handle element 106 relative to the obtained ultrasound data 124. The camera 112 may include a light source 114 and a fixed pattern 116 on, for example, a glass scale. A shadow of the fixed pattern 116 is cast on and detected by a sensor 128 of the first handle 106 to provide a first handle data 132 including data corresponding to a position and/or orientation of the first handle 106 relative to the ultrasound device 102 in up to six dimensions. Using the collected data, the tracking station 104 is able to register (e.g., correlate) the ultrasound data 124 with the CT data 126 to determine a location of the first handle element 106 relative to the CT data 126. Once registration has been complete, the bone may be manipulated according to an exemplary system and method according to the invention, as described in greater detail below.

The first handle element 106 is positioned on a first portion of the bone while a second handle element 108 is positioned on a second portion of the bone. The second handle element 108 includes a light emitting apparatus 130, such as an LED array, which communicates with the sensor 128 on the first handle element 106 to provide second handle data 134 indicating a location of the second handle element 108 relative to the first handle element 106. The tracking station 104 uses the second handle data 134 to determine a location of the second handle element 108 relative to the CT data 126 and displays the locations of the first and/or second handle elements 106, 108 on a display 120 relative to the CT data 126. As will be described in greater detail below with respect to FIGS. 2-6, the first and second handle elements 106, 108 are initially positioned on a rigid bone and subsequently cut after registering the positions thereof. As the first and second handle elements 106, 108 are manipulated by a user and moved relative to one another, the corresponding motion of the first and second portions of bone relative to one another is tracked and the CT data 126 is manipulated to display this relative motion. That is, portions of the image represented by the CT data 126 corresponding to the first and second portions of the bone are moved relative to one another based on the second handle data 134 so that a user sees on the display 120 the motion of the first and second portions of bone in real time.

The scanner 110 of the ultrasound device 102 may take a 2D or 3D image of the bone to obtain ultrasound data 124. The tracking station 104 then looks through the ultrasound data 124 for portions bearing similarity of contour to portions of the image represented by the CT data 126 to identify portions of the ultrasound data 124 and the CT data 126 corresponding to the same portion of the bone. The ultrasound data 124 and the CT data 126 may have several points of similarity requiring the ultrasound device 102 to take several ultrasound images over discrete periods of time to ensure correct registration between these identified portions of data representing the same portion of the bone. A number of 2D images required may, for example, depend on the homogeneity of the contour of the bone and a level of detail in the ultrasound and CT data 124, 126. Thus, several candidate locations of the CT data 126 may be identified and additional ultrasound data 120 collected until one of the several candidate locations is confirmed as correctly corresponding to a selected portion of the image represented by the CT data 126.

As would be understood by those skilled in the art, the first handle element 106 may be sized and shaped to be gripped by a surgeon or other user so that the first portion of bone, on which the first handle element 106 is mounted, may be manipulated via motion of the first handle element 106. The first handle element 106 includes the sensor 128 therein providing first handle data 132, and which includes data regarding a relative position and/or orientation between the first handle element 106 and the ultrasound device 102. The sensor 128 detects a shadow cast thereon via the light source 114 and fixed pattern 116 of the ultrasound device 102. A size and/or distortion of the pattern of the shadow is used to determine a position and orientation of the first handle element 106 relative to the ultrasound device 102 in 6 dimensions. This first handle data 132 is transmitted to the tracking station 104 to determine the location of the first handle element 106 relative to the CT data 126.

The second handle element 108 is also sized and shaped to be gripped by the user so that the second portion of bone on which the second handle element 108 is mounted may be manipulated via the second handle element 108. The second handle element 108 includes a light emitting apparatus 130 such as, for example, an LED array, providing second handle data 134, which includes data regarding a relative position between the first and second handle elements 106, 108. The light emitting apparatus 130 is configured to communicate with the sensor 128, which detects light from the apparatus 130, to determine a position and orientation of the second handle element 108 relative to the first handle element 106 in 6 dimensions. This second handle data 134 is transmitted to the tracking station 104. Since the location of the first handle element 106 is known relative to the CT data 126, the tracking station 104 uses the relative position and orientation between the first and second handle elements 106, 108 to determine a location of the second handle element 108 relative to the CT data 126.

In another embodiment of the invention, the relative tracking between the first and second handle elements 106, 108 may be provided by a field generator (not shown) provided on one of the first and second handle elements 106, 108, the field generator communicating with a field sensor (not shown) provided on the other of the first and second handle elements 106, 108.

The tracking station 104 may be a computer or other processing arrangement including a processor 118 and a display 120. The ultrasound data 124, the CT data 126, the first handle data 132 and the second handle data 134 may, for example, be saved on a memory 122 of the tracking station 104 and may be used to register the first handle element 106 to the CT data 126. The processor 118 correlates the ultrasound data 124 and the CT data 126, and uses the first handle data 132 to determine a location of the first handle element 106 relative to the CT data 126. The processor 118 may similarly determine a location of the second handle element 106 relative to the CT data 126. The locations of the first and second handle elements 106, 108 maybe displayed on the display 120 relative to the image represented by the CT data 126 in real time. Thus, a user may be provided with real time information regarding the completion of the registration process and/or the treatment of the bone. It will be understood by those of skill in the art, the tracking station 104 may be a distributed system. For example, the memory and processor may be located in a server, which is communication with a display in the operating room.

Once the locations of both the first and second handle elements 106, 108 have been determined relative to the image represented by the CT data 126, the surgeon may move the first and second portions of the bone relative to one another using the first and second handle members 108. Relative movement between the first and second handle elements 106, 108 may be continuously tracked and monitored such that a manipulated CT image showing the relative motion between the first and second portions of bone may be displayed on the display 120. Thus, the surgeon may view the manipulated CT image on the display 120 to move the portions of bone until a desired spatial relationship between the portions of bone is obtained.

Figure 3:
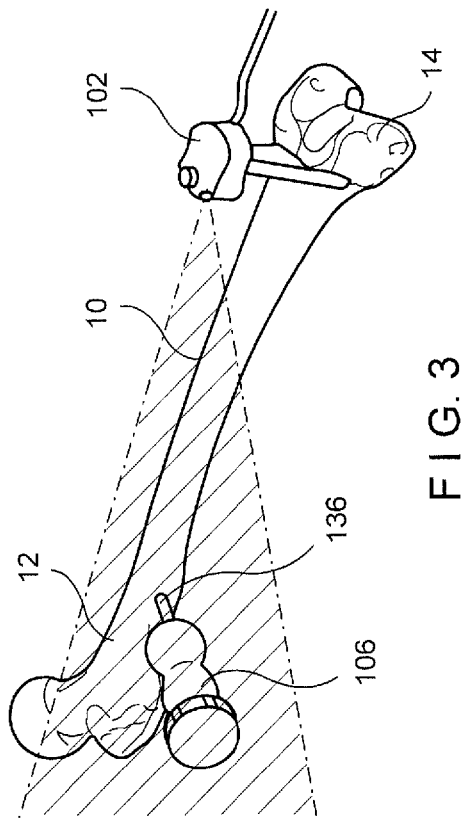
FIG. 3 shows a perspective view of the bone of FIG. 2 with a first handle element attached to a first portion thereof.
Figure 2:
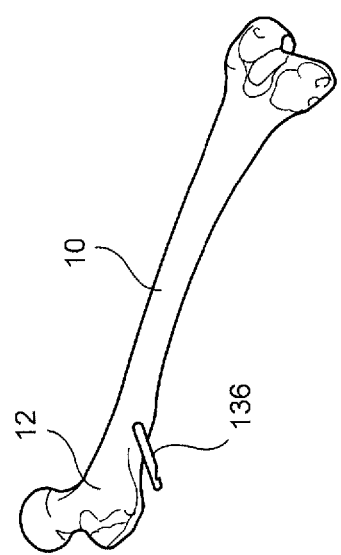
FIG. 2 shows a perspective view of a bone on which an osteotomy procedure is to be performed according to an exemplary embodiment of the present invention, using the system of FIG. 1.
Figure 4:
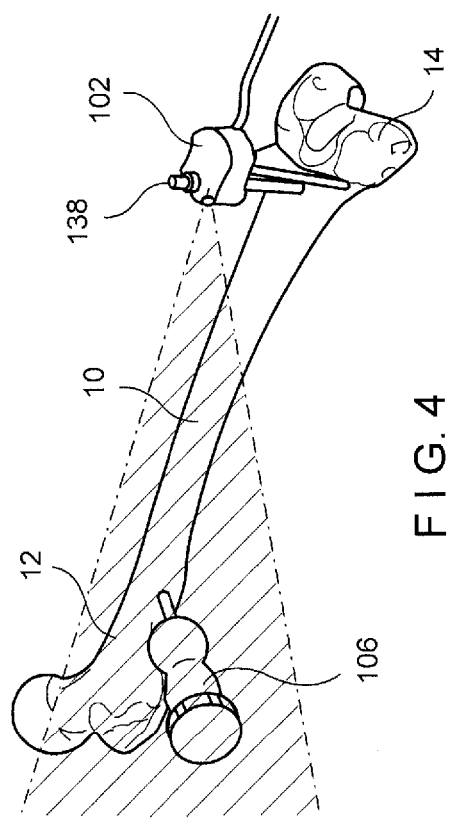
FIG. 4 shows a perspective view of the bone of FIG. 2 with a marker inserted into a second portion thereof.

The system 100 may be used in a variety of different bone treatment procedures. In one exemplary embodiment, as shown in FIGS. 2-6, the system 100 is used in performing an osteotomy of a bone 10, in which the bone 10 is cut to shorten, lengthen or change an alignment thereof. A CT image of the bone 10 is taken prior to the osteotomy procedure and the CT data 126 obtained therefrom is transmitted to the tracking station 104. As shown in FIG. 2, a first marker 136 is positioned in a first portion 12 of the bone 10. The term "marker used throughout should be understood as meaning any suitable bone marker such as, for example, a K-wire, shunt screw, pin or other bone fixation element that has a desired rigidity and rotational stability, as those of skill in the art will understand. The first handle element 106 is then mounted over the first marker 136, as shown in FIG. 3, and the ultrasound device 102 positioned over a portion of the bone 10 to obtain ultrasound data 124 and first handle data 132. The ultrasound data 124 and the first handle data 132 are transmitted to the tracking station 104 and the processor 118 automatically registers the ultrasound data 124 to the CT data 126. The ultrasound data 124 may be obtained from one or more 3D ultrasound images of the bone 10. Using a drill-guide (not shown) attached to the scanner 110, a second marker 138 is inserted into another portion of the bone 10 to permit relative tracking between the first and second portions of the bone, as will be described in greater detail later on. The tracking station 104 then looks through the ultrasound data 124 from the 3D ultrasound for portions bearing similarity of contour to portions of the image represented by the CT data 126 to identify portions of the ultrasound data 124 and the CT data 126 corresponding to the same portion of the bone. Specifically, the second marker 138 is inserted into a second portion 14 of the bone 10, as shown in FIG. 4. The second marker 138 is inserted into the second portion 14, for example, through an opening in the ultrasound device 102 such that the second marker is guided therethrough. Alternatively, the second marker 138 may be positioned in the second portion 14 free-hand, without being guided through the ultrasound device 102. As will be described in greater detail later on, such an embodiment requires that the second marker 138 be located via the ultrasound device 102 after implantation. As shown in FIG. 5, the second handle element 108 may be mounted over the second marker 138 to prevent rotation thereof. Using the location of the first handle element 106 on the first marker 136 and the location of the second marker 138, a location of the first handle element 106 relative to the CT data 126 using the first handle data 132 is registered. The CT image represented by the CT data 126 and the location of the first handle element 106 thereon are displayed on the display 120. The light emitting apparatus 130 of the second handle element 108 then communicates with the sensor 128 of the first handle element 106 to provide the second handle data 134 (i.e., data regarding a relative position between the first and second handle elements 106, 108) to the tracking station 104. Using the second handle data 134, the processor 118 determines a location of the second handle element 108 relative to the CT data 126. The location of the second handle element 108 is then displayed on the CT image on the display 120. As those skilled in the art will understand, the use of a 3D ultrasound permits the use of the 3D ultrasound data 124 to build up corresponding CT data 126 for registration without having to track a position of the scanner 110.

As shown in FIG. 6, the surgeon then makes a cut 16 in the bone 10, between the first and the second portions 12, 14 freeing the first and second portions of bone 12, 14 to move relative to one another via manipulation of the first and second handle elements 106, 108. The processor 118 tracks the relative movement therebetween and produces a manipulated CT image on the display 120 showing the relative movement in real-time so that the surgeon may manipulate the first and second handle elements 106, 108 until the first and second portions 12, 14 of the bone are aligned, as desired.

Figure 7:
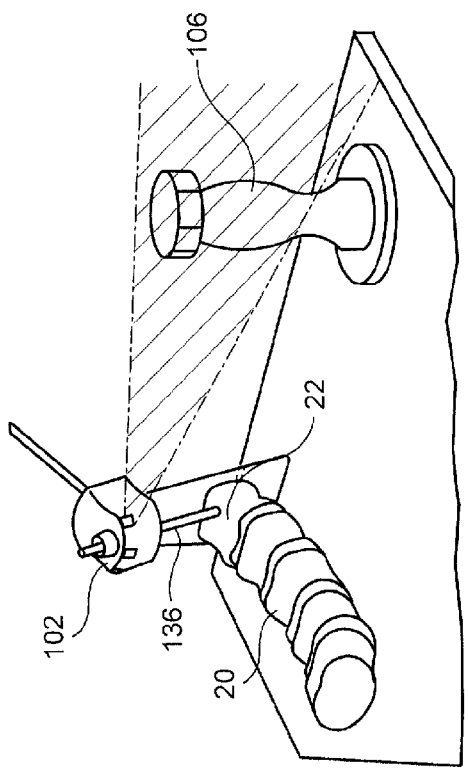
FIG. 7 shows a perspective view of a portion of a spine on which a procedure to treat scoliosis is performed according to another exemplary embodiment of the present invention, using the system of FIG. 1.
Figure 8:
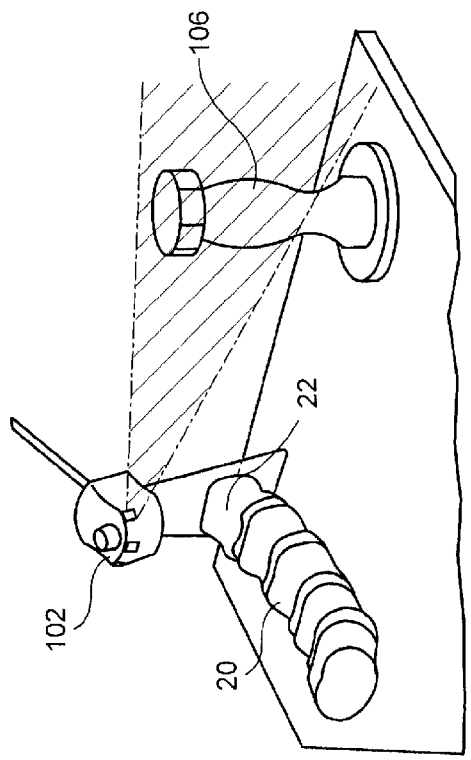
FIG. 8 shows a perspective view of the spine of FIG. 7, with a marker inserted into a first vertebra thereof.
Figure 9:
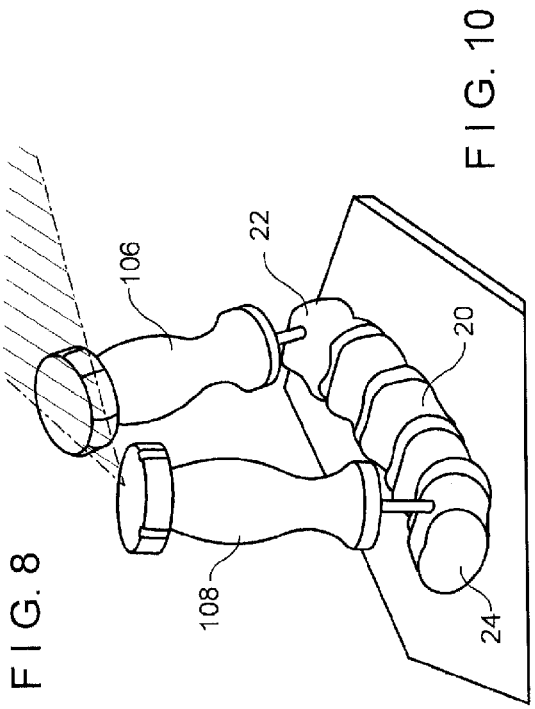
FIG. 9 shows a perspective view of the spine of FIG. 7, with a first handle element mounted over the marker.

In another exemplary embodiment, as shown in FIGS. 7-10, the system 100 is used to treat a patient with scoliosis. Similarly to the osteotomy procedure described above, a CT image of a portion of a spine 20 is obtained prior to the procedure and the CT data 126 is transmitted to the tracking station 104. As shown in FIG. 7, a reference device, which may be a first handle element 106, may be positioned proximate the spine 20 without being attached thereto. The ultrasound device 102 is then used to obtain ultrasound data 124 of a first vertebra 22 of the spine 20 while also communicating with the sensor 128 of the first handle element 106 to provide first handle data 132 to the tracking station 104. The ultrasound data 124 may be obtained from one or more 2D ultrasound images of the first vertebra 22. The processor 118 registers the ultrasound and CT data 124, 126 and determines first handle data 132 which may be used to track a drill-guide used in the scoliosis treatment procedure, wherein the drill-guide may be attached to the ultrasound scanner 110. Specifically, the ultrasound scanner 110 used in the present embodiment is tracked in three dimensions to build up a 3D set of ultrasound data 124 (i.e., using the tracking station 104 to look through the ultrasound data 124 for portions bearing similarity of contour to portions of the image represented by the CT data 126 to identify portions corresponding to the same portion of the bone) using the reference device to provide position and orientation data. The registered CT image represented by the CT data 126 is displayed on the display 120. As shown in FIG. 8, a first marker 136 is inserted, for example, through an opening in the ultrasound device 102 into the first vertebra 22 and, using the reference point, the location on the first vertebra 22 at which the first marker 136 is inserted is established. The first handle element 106, which was used as the reference point, is then positioned over the first marker 136. Since a location of the first marker 136 is known, the location of the first handle element 106 relative to the CT data 126 can be registered. It will be understood by those of skill in the art, that the first vertebra 22 may be drilled prior to insertion of the first marker 136 to facilitate insertion thereof. The first handle 106 is then mounted over the first marker 136, as shown in FIG. 9. Since the location of the first handle 106 relative to the CT data 126 has been determined, placement of the first handle 106 relative to the first vertebra 22 is tracked by the processor 118 and shown on the display 120.

Figure 10:
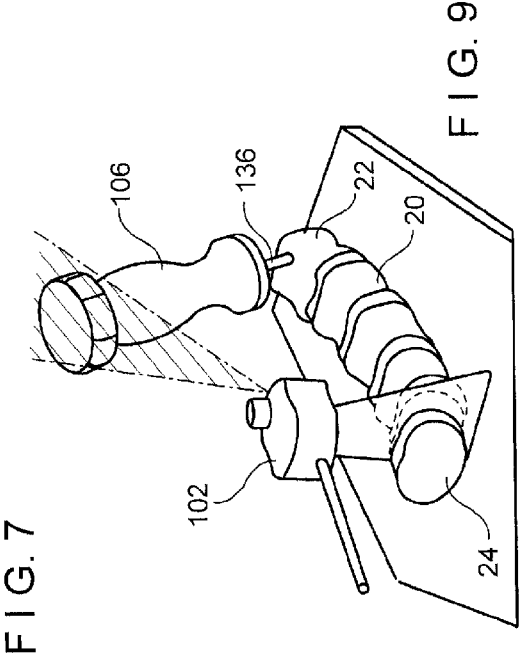
FIG. 10 shows a perspective view of the spine of FIG. 7, with a second handle element attached to a second vertebra thereof.

The ultrasound device 102 is then be positioned over a second vertebra 24 to obtain ultrasound data 124 for the second vertebra 24. Similarly, the ultrasound data 124 of the second vertebra 24 may be obtained from one or more 2D ultrasound images thereof. The ultrasound device 102 may also communicate with the first handle element 106 to determine a position and orientation thereof relative to the first handle element 106. Data relating to the ultrasound data 124 of the second vertebra 24 and the position of the ultrasound device 102 is transmitted to the tracking station 104 to register the ultrasound data 124 of the second vertebra 24 to the CT data of the spine 20. The second handle element 108 is attached to the second vertebra 24, as shown in FIG. 10, and communicates with the first handle element 106 to provide second handle data 134 to the tracking station 104. The processor 118 uses the second handle data to determine a location of the second handle 108 relative to the CT data 126, which may be displayed on the display 120. Once locations of both the first and second handles 106, 108 have been determined relative to the CT data 126, first and second vertebra 22, 24 may be moved relative to one another via the first and second handles 106, 109 to manipulate alignment of the spine 20. The tracking station 104 continuously tracks and monitors movement of the spine 20 to display a manipulated CT image thereon which corresponds to movement of the first and second vertebrae 22, 24 relative to one another to facilitate a desired alignment of the spine 20.

Figure 11:
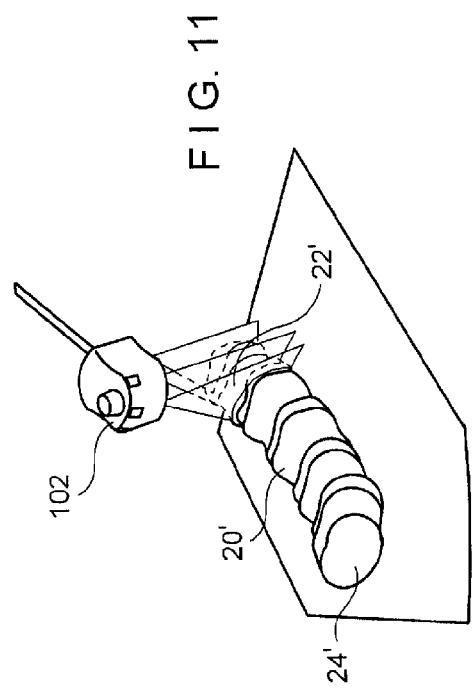
FIG. 11 shows a perspective view of a portion of a spine to be treated using a scoliosis procedure according to an alternate embodiment of the present invention, using the system of FIG. 1.
Figure 12:
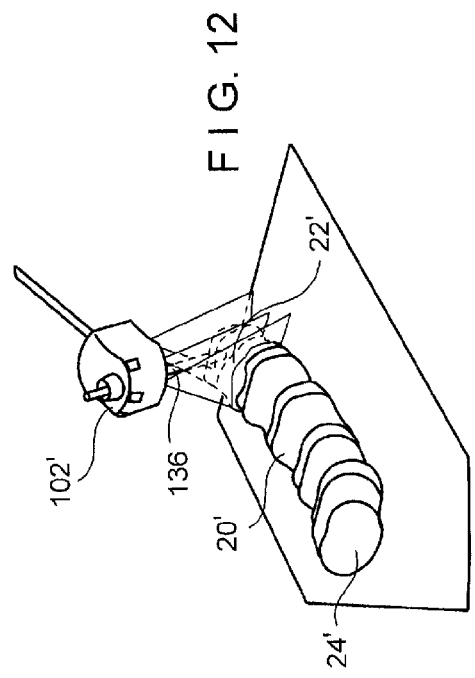
FIG. 12 shows a perspective view of the spine of FIG. 11, with a first marker inserted into a first vertebra thereof.
Figure 13:
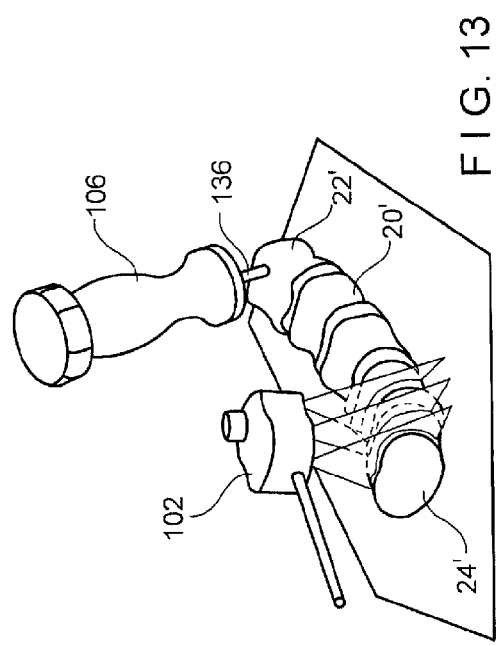
FIG. 13 shows a perspective view of the spine of FIG. 11, with an ultrasound device scanning a second vertebra thereof.
Figure 14:
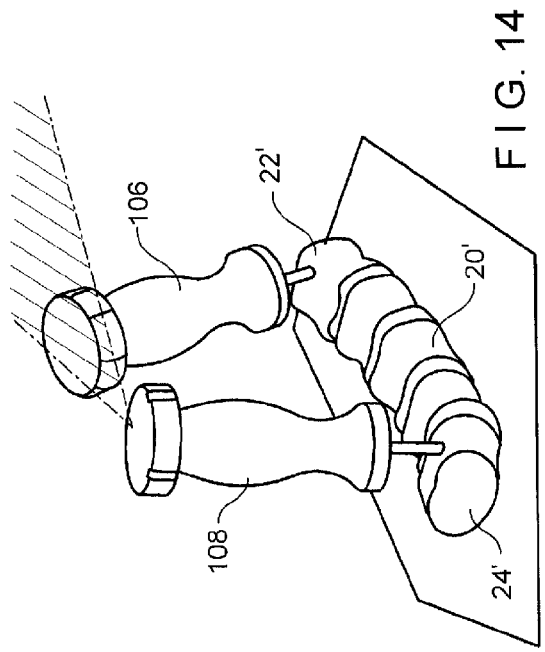
FIG. 14 shows a perspective view of the spine of FIG. 11, with first and second handle elements attached to the first and second vertebra, respectively.

FIGS. 11-14 show an alternate embodiment for treating scoliosis of a spine 20', which is substantially similar to the embodiment described above except as pointed out below. As shown in FIG. 11, the ultrasound device 102 is positioned over a first vertebra 22' to obtain ultrasound data 124 of the first vertebra 22' which is registered with previously obtained CT data 126 of the spine 20'. The ultrasound data 124, however, may be obtained from a 3D ultrasound image of the first vertebra 22'. A first marker 136 may then be then inserted into the first vertebra 22', as shown in FIG. 12, through an opening of the ultrasound device 102. The first handle element 106 is mounted over the first marker 136, as shown in FIG. 13, and the location of the first handle element 106 determined relative to the CT data 126. The ultrasound device 102 is then positioned over a second vertebra 24' to obtain ultrasound data 124 for the second vertebra 24' using, for example, a 3D ultrasound image, and to communicate with the first handle element 106 to provide first handle data 132 to the tracking station 104. The processor 118 registers the ultrasound data 124 of the second vertebra 24' with the CT data 126 of the spine 20' and determines a location of the first handle 106 relative to the CT data 126. The second handle element 108 is then attached to the second vertebra 24', as shown in FIG. 14, to communicate with the first handle element 106 and provide second handle data 134 (i.e., data regarding a position and orientation of the second handle element 108 relative to the first handle element 106) to the tracking station 104. The processor 118 uses the collected data to determine a location f the second handle element 108 relative to the CT data 126. The locations of the first and second handle elements 106, 108 relative to the CT data 126 may be shown on the display 120, in real-time, so that the surgeon may move the first and second vertebra 22', 24' relative to one another via the first and second handles 106, 108. The relative movement between the first and second handles 106, 108 produces a manipulated CT image on the display 120 so that the surgeon may move the first and second vertebra 22', 24' into a desired spatial relationship relative to one another by viewing the manipulated image.

As shown in FIGS. 15-18, the system 100 may also be used to treat a fractured bone 30 according to another exemplary embodiment of the present invention. As shown in FIG. 15, the ultrasound device 102 is positioned over a first fractured portion 32 of the bone 30 to obtain ultrasound data 124 of the first fractured portion 32. In particular, the ultrasound device 102 may utilize 3D imaging to obtain the ultrasound data 124, which may be registered with previously obtained CT data 126 of the bone 30. The first marker 136 may be inserted through an opening in the ultrasound device 102 and into the first fractured portion 32, such that a location of the first handle 106, when mounted over the first marker 136 is known relative to the CT data 126. As shown in FIG. 16, the process may be repeated for a second fractured portion 34 to obtain ultrasound data 124 for the second fractured portion, which may be registered with the CT data 126 of the bone 30. As shown in FIG. 17, a second marker 138 may be inserted into the second fractured portion 34 via the opening in the ultrasound device 102. The first and second handle elements 106, 108 may be mounted over the first and second markers 136, 138, respectively, as shown in FIG. 18, and the CT data 126 including the locations of the first and second handle elements 106 relative thereto, may be displayed on the display 120. The first and second handle elements 106, 108 may continue to communicate with one another to determine a position relative to one another so that relative movement thereof is tracked and displayed as a manipulated CT image on the display 120. Thus, the first and second fractured portions 32, 34 may be moved relative to one another, as desired, by viewing the manipulated CT image on the display 120.

The systems depicted in FIGS. 1-18 have been described as using CT-ultrasound registration to identify marker locations and set up the handles so that manipulation can be performed. However, as those skilled in the art will understand, any marker registration process may be used to establish the marker locations. For example, the markers may be positioned in a bone and then a CT scan performed to obtain location information of the markers on the bone.

It will be apparent to those skilled in the art that various modifications and variations can be made in the structure and the methodology of the present invention, without departing from the spirit or the scope of the invention. Thus, it is intended that the present invention come within the scope of the appended claims and their equivalents.

What is claimed is:

1. An assembly for manipulating a bone, comprising:
a first manipulating element configured to be attached to a first portion of bone and including a location emitting signal;
a second manipulating element configured to be attached to a second portion of bone and including a sensor detecting the location emitting signal to provide a position and orientation signal of the first and second manipulating elements relative to one another; and
a tracking unit including a processor tracking movement of the first and second manipulating elements relative to one another in a plurality of dimensions using the position and orientation signal.

2. The assembly of claim 1, wherein the first and second manipulating elements include a handle sized and shaped to be gripped by a user to move the first and second portions of bone, respectively.

3. The assembly of claim 1, wherein the location emitting signal is a light emitting array.

4. The assembly of claim 1, wherein the location emitting signal is a field generator.

5. The assembly of claim 1, further comprising a scanning unit connected to the second manipulating element to determine a location of one of the first and second manipulating elements relative.

6. The assembly of claim 5, wherein the scanning unit includes a light source which casts a shadow of a fixed pattern thereof to be detected by the sensor of the first manipulating element such that a position and orientation of the first manipulating element relative to the scanning unit is determined.

7. The assembly of claim 3, further comprising a display showing a location of one of the first and second manipulating elements relative to the surface data of the bone.

8. The assembly of claim 1, wherein the first and second manipulating elements are markers.

9. A method for tracking a manipulation of a bone, comprising:
attaching a first manipulating element to a first portion of bone, the first manipulating element emitting a location signal;
attaching a second manipulating element to a second portion of bone, the second manipulating element sensing the location signal to provide a sensed location;
determining a position and orientation of a first manipulating element relative to a second manipulating element in a plurality of dimensions; and
tracking relative movement between the first and second manipulating elements by detecting changes in the emitted location signal and the sensed location.

10. The method of claim 9, further comprising displaying a location of the first and second manipulating elements relative to the surface data.

11. The method of claim 10, further comprising generating a manipulated surface image showing a movement of the first and second portions of bone via manipulation of the first and second manipulating elements relative to one another.

12. The method of claim 9, wherein the relative tracking between the first and second manipulating elements is performed via one of a light emitting apparatus and a field generator.

* * * * *